United States Patent
Tian et al.

(10) Patent No.: US 12,428,784 B2
(45) Date of Patent: *Sep. 30, 2025

(54) METHOD FOR PREPARING UNBLEACHED BIOMECHANICAL PULP BY HOT STEAM IN COORDINATION WITH BIOLOGICAL ENZYME TREATMENT OF WHEAT STRAW AND FULL UTILIZATION OF BY-PRODUCTS THEREOF

(71) Applicant: Qilu University of Technology, Jinan (CN)

(72) Inventors: Zhongjian Tian, Jinan (CN); Xingxiang Ji, Jinan (CN); Dongxing Wang, Jinan (CN); Wenjia Han, Jinan (CN); Hao Ma, Jinan (CN); Xuejun Shao, Jinan (CN)

(73) Assignee: Qilu University of Technology, Jinan (CN)

( * ) Notice: Subject to any disclaimer, the term of this patent is extended or adjusted under 35 U.S.C. 154(b) by 951 days.

This patent is subject to a terminal disclaimer.

(21) Appl. No.: 17/561,158

(22) Filed: Dec. 23, 2021

(65) Prior Publication Data

US 2022/0205176 A1    Jun. 30, 2022

(30) Foreign Application Priority Data

Dec. 31, 2020  (CN) .......................... 202011639138.8

(51) Int. Cl.
| | | |
|---|---|---|
| *D21C 5/00* | (2006.01) | |
| *C05F 7/02* | (2006.01) | |
| *C12P 1/00* | (2006.01) | |
| *D21C 1/02* | (2006.01) | |
| *D21C 1/06* | (2006.01) | |
| *D21C 11/00* | (2006.01) | |
| *D21C 11/10* | (2006.01) | |
| *D21D 1/30* | (2006.01) | |
| *D21H 11/12* | (2006.01) | |

(52) U.S. Cl.
CPC ................ *D21C 5/005* (2013.01); *C05F 7/02* (2013.01); *C12P 1/00* (2013.01); *D21C 1/02* (2013.01); *D21C 1/06* (2013.01); *D21C 11/0007* (2013.01); *D21C 11/10* (2013.01); *D21D 1/306* (2013.01); *D21H 11/12* (2013.01); *C12P 2201/00* (2013.01)

(58) Field of Classification Search
CPC ............. D21C 1/06; D21C 1/02; D21C 5/005
See application file for complete search history.

(56) References Cited

U.S. PATENT DOCUMENTS

| | | | | |
|---|---|---|---|---|
| 10,087,476 B2* | 10/2018 | Foody | ................ | D21C 11/0007 |
| 10,240,171 B2* | 3/2019 | Baets | ....................... | D21C 1/06 |
| 11,624,154 B2* | 4/2023 | Chen | ....................... | D21C 1/06 |
| | | | | 162/91 |
| 11,834,784 B2* | 12/2023 | Ji | ........................... | D21H 11/18 |
| 2005/0241785 A1* | 11/2005 | Peng | ...................... | D21B 1/021 |
| | | | | 162/96 |

FOREIGN PATENT DOCUMENTS

| | | | | |
|---|---|---|---|---|
| CN | 101787656 A | 7/2010 | | |
| CN | 109706771 A | 5/2019 | | |
| WO | WO-2009056017 A1 * | 5/2009 | .............. | C05F 11/00 |

* cited by examiner

*Primary Examiner* — Anthony Calandra
(74) *Attorney, Agent, or Firm* — Flener IP & Business Law; Zareefa B. Flener

(57) ABSTRACT

The disclosure relates to a method for preparing unbleached biomechanical pulp by hot steam and biological enzyme treatment and full utilization of by-products thereof, and belongs to the technical field of papermaking technology and comprehensive utilization of waste. The present disclosure proposes a method for preparing high-strength unbleached biomechanical pulp, using whole wheat straw as a raw material, by using hot water in coordination with an alkaline biological enzyme to treat whole wheat straw, thereby meeting the requirements for the production of unbleached linerboard and paper-based materials, and recycling by-products thereof to prepare biomass compound fertilizers, which creates wealth from solid waste and realizes the high-value full utilization of wheat straw. The preparation method of the disclosure is simple, green, clean and efficient, and has good practical application value and broad application prospects.

9 Claims, No Drawings

METHOD FOR PREPARING UNBLEACHED BIOMECHANICAL PULP BY HOT STEAM IN COORDINATION WITH BIOLOGICAL ENZYME TREATMENT OF WHEAT STRAW AND FULL UTILIZATION OF BY-PRODUCTS THEREOF

CROSS REFERENCE TO RELATED APPLICATION

This patent application claims the benefit and priority of Chinese Patent Application No. 202011639138.8 filed on Dec. 31, 2020, the disclosure of which is incorporated by reference herein in its entirety as part of the present application.

TECHNICAL FIELD

The disclosure belongs to the technical field of papermaking technology and waste comprehensive utilization, and particularly relates to a method for preparing unbleached biomechanical pulp by hot steam in coordination with a biological enzyme and full utilization of by-products thereof.

BACKGROUND ART

Disclosure of the background information is only intended to increase the understanding of the overall background of the present disclosure, and is not necessarily regarded as an acknowledgement or any form of suggestion that the information constitutes the prior art known to those of ordinary skill in the art.

In traditional pulping and papermaking, wheat straw, as a representative of grasses, is an important raw material for papermaking. However, because wheat straw leaves and sheaths are not easily pulped, only wheat straw are usually retained during the preparation process, while wheat straw leaves and sheaths are required to remove as much as possible. The removal of wheat straw leaves and wheat straw sheaths not only increases the cost of material preparation, but also greatly reduces the utilization rate of wheat straw as raw materials. To this end, the applicant proposes a preparation process for preparing unbleached biomechanical pulp from wheat straw by treating with hot water in coordination with an alkaline biological enzyme, in which wheat straw is used as raw material, and high-strength unbleached biomechanical pulp is prepared by treating whole wheat straw with hot water in coordination with an alkaline biological enzyme method (see CN 109706771A). However, the problem of by-products produced in the pulping process has not been well resolved, which is unfavorable to the comprehensive high-value utilization of agricultural straw.

SUMMARY

In view of the background above, the present disclosure proposes a method for preparing unbleached biomechanical pulp and by-products by treating wheat straw with hot steam and a biological enzyme. The present disclosure proposes a method for preparing high-strength unbleached biomechanical pulp by using whole wheat straw as a raw material and treating the whole wheat straw with hot water and an alkaline biological enzyme, thereby meeting the requirements for producing unbleached packaging paper and paper-based materials, and recycling by-products thereof to prepare biomass compound fertilizers. It creates wealth from solid waste and realizes the high-value full utilization of wheat straw. The preparation method of the disclosure is simple, green, clean and efficient, and has good practical application value and broad application prospects.

The specific technical solutions are as follows:

In a first aspect of the present disclosure, there is provided a method for preparing unbleached biomechanical pulp by treating wheat straw by hot steam in coordination with biological enzyme treatment and full utilization of by-products thereof, wherein the method comprises the following steps:

(1) taking a waste wheat straw after wheat grain harvest as a raw material, mixing water with the wheat straw at a liquid ratio of 1:3-1:6, adding a trace of KOH to adjust a pH of a mixture of the wheat straw and the water to 10-14, and then charging hot steam whose temperature is 100-120° C. for treatment for 15-60 min; collecting a waste lye and decaying leaves and straw that cannot be used for processing;

(2) extruding and splitting the wheat straw treated with the hot steam; collecting wastewater from an extrusion stage;

(3) reacting the split wheat straw with an alkaline biological complex enzyme at a temperature of 40-60° C. for 30-90 min; collecting wastewater generated in an enzyme treatment stage; and (4) refining the wheat straw undergone the above treatments, and collecting a refining washing water;

treating the waste lye, the wastewater from the extrusion stage, the wastewater generated in the enzyme treatment stage, and the refining washing water with a multi-effect evaporator to evaporate and concentrate to obtain a residue, and recycling heat energy for a hot water vapor pretreatment stage of step (1); mixing the residue with the decaying leaves and straw that cannot be used for processing in step (1) and adjusting pH thereof for fertilizer production.

In a second aspect of the present disclosure, a biomechanical pulp and/or fertilizer prepared by the above method is provided.

In a third aspect of the present disclosure, the use of the biomechanical pulp in the preparation of linerboard and/or the use of the fertilizer in promoting the growth of crops is provided.

The beneficial effects of one or more of the above embodiments:

The above embodiments, using wheat straw waste as raw materials and adopting biotechnological and mechanical methods, develop an excellent biomechanical pulp preparation method that ensures the recycling of papermaking wastewater, without increasing wastewater discharge and causing environmental pollution. The method solves the shortage of papermaking fiber raw materials to a large extent. At the same time, agricultural residues can be used with high added value, which may effectively access the "agriculture, rural areas and farmers" issues, eliminate the incineration of crop waste from the source, and achieve both economic and social benefits.

In the conventional pulping and papermaking process, wheat leaves of the wheat straw are removed and only the wheat straw stalks are used. For addressing the problem of whole wheat wastes (wheat straw, wheat leaves and leaf sheaths), a full utilization technology of the waste after wheat harvesting is proposed for the first time. A new concept of hot steam saturation and softening, unbleached biomechanical pulp is proposed; a new process and technology for preparing high-strength unbleached biomechanical pulp by hot steam in coordination with alkaline complex biological enzymes is proposed for the first time. Compared with conventional method for preparing mechanical pulp, this technology is more effective. It saves more than 40% of energy consumption for refining, and various physical indicators thereof meet the requirements for the production of packaging paper and paper-based materials. In particular, it has a wide range of applications in linerboard packaging materials.

The waste of crop wheat is used as a raw material for pulping, the wheat straw is treated with atmospheric hot steam water vapor, and at the same time a trace alkali is added to adjust the pH of the wheat straw water to 10-14. After some hemicellulose, lignin, pectin, etc. in the wheat straw are dissolved and the wheat straw is saturated and softened by the hot steam, the wheat straw is subjected to spiral extrusion treatment to be physically split, and then undergo biological enzyme treatment. After the biological enzyme treatment, the fiber is further softened, and then the wheat straw is refined to produce unbleached packaging paper, such that the requirements of paper-based materials is met. Particularly, the method has a wide range of applications in linerboard and packaging corrugated paper.

In the above embodiments, the wastewater produced in each stage is treated by a multi-effect evaporator. While the solid residue is recycled, the pH of which is adjusted with a trace of phosphoric acid. It is then granulated to make a biomass compound fertilizer. The fertilizer contains an appropriate amount of K, P element and a large number of easily degradable, small-particle straw components (such as hemicellulose, etc.), the entire production process is green and environmentally friendly, and the high-value and full utilization of wheat straw is realized. It should be noted that, unlike the preparation of fertilizers using conventional chemical pulp (chemical pulp requires high temperature and high alkalinity, the general temperature is above 160° C., and the amount of alkali used is about 20%) by-product, the embodiments herein thus naturally have "innate advantages" in fertilizer preparation, as the straw used therein is a good material for natural potassium fertilizer. At the same time, after the process conditions are optimized and screened, the biomass compound fertilizer prepared in this disclosure also has advantages of high fertilizer effects, good storage stability and the like.

In summary, the above-mentioned embodiments are simple in preparation, energy conservative and environmental protective, which conforms to the national industrial policies for resource conservation, economic recycle, energy conservation and emission reduction, and can produce good social, economic and ecological benefits, and thus they have good practical application value and Prospects for industrial applications.

DETAILED DESCRIPTION OF THE EMBODIMENTS

It should be pointed out that the following detailed descriptions are all exemplary and are intended to provide further description of the present disclosure. Unless otherwise specified, all technical and scientific terms used herein have the same meaning as commonly understood by those of ordinary skill in the technical field to which the present disclosure belongs.

It should be noted that the terms used herein are only for describing specific embodiments, and are not intended to limit the exemplary embodiments according to the present disclosure. As used herein, unless the context clearly indicates otherwise, the singular form is also intended to include the plural form. In addition, it should also be understood that when the terms "comprising" and/or "including" are used in this specification, they indicate that there are features, steps, operations, and/or combinations thereof.

As used herein, the term "liquid ratio" refers to a cooking liquid ratio of the raw material, and specifically refers to a ratio of the weight of a cooking absolutely dry raw material to a total cooking liquid volume.

In a first exemplary embodiment of the present disclosure, a method for preparing unbleached biomechanical pulp by treating wheat straw by hot steam in coordination with biological enzyme treatment and full utilization of by-products thereof, wherein the method comprises the following steps:

(1) taking a waste wheat straw after wheat grain harvest as a raw material, mixing water with the wheat straw at a liquid ratio of 1:3-1:6, adding a trace of KOH to adjust a pH of a mixture of the wheat straw and the water to 10-14, and then charging hot steam whose temperature is 100-120° C. for treatment for 15-60 min; collecting a waste lye and decaying leaves and straw that cannot be used for processing;

(2) extruding and splitting the wheat straw treated with the hot steam; collecting wastewater from an extrusion stage;

(3) reacting the split wheat straw with an alkaline biological complex enzyme at a temperature of 40-60° C. for 30-90 min; collecting wastewater generated in an enzyme treatment stage; and (4) refining the wheat straw undergone the above treatments, and collecting a refining washing water;

treating the waste lye, the wastewater from the extrusion stage, the wastewater generated in the enzyme treatment stage, and the refining washing water with a multi-effect evaporator to evaporate and concentrate to obtain a residue, and recycling heat energy for a hot water vapor pretreatment stage of step (1); mixing the residue with the decaying leaves and straw that cannot be used for processing in step (1) and adjusting pH thereof for fertilizer production.

In step (1), the waste wheat straw as a raw material may be cut into 3-6 cm in length, and air-dried.

In step (1), the liquid ratio may be 1:3-1:6 (g/mL), which is determined by a lot of experimentation and analysis. A solution with the liquid ratio will form a wheat straw solution with a specific pH after a certain period of time, thus making a pH of a prepared biomechanical pulp neutral.

In step (1), the hot steam may be used to perform a specific treatment on the wheat straw to make fibers of the wheat straw softer. Compared with other methods, it may prepare linerboard paper with better folding strength as confirmed by experimentation.

In step (1), the KOH may be added to adjust a pH of the wheat straw water to 10-14. The purpose of adding KOH is, on the one hand, to make a small part of hemicellulose, lignin and pectin dissolve out from the wheat straw, and on the other hand, to assist the hot steam softening the wheat straw as soon as possible, which is the basis for the next screw extrusion; at the same time, more importantly, since potassium is a large element necessary for plants, potash treatment is used herein to make the subsequent fertilizers rich in potassium.

In step (1), a temperature of the hot steam for treatment may be 100-120° C., and a time thereof may be 15-60 min. When the temperature is too low, the whole wheat straw waste cannot be effectively softened by absorbing water, which will affect a subsequent splitting effect as confirmed by experimentation.

In step (2), a screw extruder may be used for extrusion and splitting, and a process condition may be: a compression ratio of the screw extruder being 1:(3-6).

A resulting saturated and softened wheat straw may be subjected to a combined action of various forces such as shearing, stretching, twisting and pressing in the screw extruder, which further causes the hemicellulose in the wheat straw to dissolve, and fibers are damaged to a certain degree. A screw extrusion significantly improves permeability of a biological enzyme into the wheat straw, resulting in a better effect and a reduced dosage of the biological enzyme. It has been verified by experimentation that the compression ratio at 1:(3-6) just slightly reduces fiber length and slightly changes the long fiber components.

In step (3), a liquid ratio may be 1:3-8 (g/mL).

For specific wheat straw waste raw materials after extrusion, the alkaline biological complex enzyme for use may be a complex enzyme of a xylanase, a cellulase and a pectinase with a total dosage of 10-80 IU/mL, preferably of 10-50 IU/mL, and with a ratio of an enzyme activity of the xylanase, the cellulase and the pectinase being (0-6):(0-4):(0-1.5), none of the enzyme activity being 0, and preferably being (5-6):(2-3):1. The applicant conducted researches and unexpectedly found that by optimizing the enzyme activity ratio of the biological complex enzyme, while ensuring a high performance of pulping, it also effectively improved fertilizer efficiency and storage stability of the fertilizer by balancing a subsequent addition amount of wastewater.

In step (4), times of the refining may be determined according to production needs, and the beating degree of the refining may be 25-50° SR.

Refining process conditions may be as follows: a KPF high-consistency disc refiner may be used for high-consistency refining, a spindle speed may be 3000-4000 r/min, a one- or two-stage refining may be conducted, and a refining gap may be 0.15-0.5 mm.

In which, a mass ratio of the waste lye, the wastewater from the extrusion stage, the wastewater generated in the enzyme treatment stage, and the refining washing water may be 5-12:1-5:1-5:5-15;

A mass ratio of the residue to the decaying leaves and straw that cannot be used for processing in step (1) may be 4-7:1-2.

A specific process of adjusting pH for fertilizer preparation is as follows: adding phosphoric acid to adjust the pH to 7, drying, pulverizing and granulating. By adopting phosphoric acid treatment, while neutralizing alkalinity, it also introduces nutrients such as phosphorus, which is more economical and environmentally friendly.

In a second exemplary embodiment of the present disclosure, a biomechanical pulp and/or fertilizer prepared by the above method is provided. The fibers in the biomechanical pulp are staggered uniformly, the fibers are soft, and length thereof is relatively long and uniform. Paper-based materials prepared from this biomechanical pulp have high burst index, tearing index and ring pressure index as indicated by the experiments below. At the same time, the fertilizer prepared by the present disclosure is a biomass compound fertilizer, which has been verified by experiments to have better fertilizer efficiency and storage stability.

In a third exemplary embodiment of the present disclosure, the use of the biomechanical pulp in the preparation of linerboard paper and/or the use of fertilizer in the promotion of crop growth is provided. Linerboard paper is mainly glued with corrugated paper core to make corrugated boxes, which are used for packaging household appliances, daily necessities, knitted cotton fabrics, stationery, Chinese patent medicines, and Western medicines, etc. The linerboard paper prepared from the above-mentioned biomechanical pulp according to the present disclosure has high breaking index, tearing index and ring pressure index, and has good folding endurance. The fertilizer prepared in the disclosure is a biomass compound fertilizer, which can effectively promote the growth of crops such as corn and wheat.

In order to enable those skilled in the art to understand the technical solutions of the present disclosure more clearly, the technical solutions of the present disclosure will be described in detail below in conjunction with specific examples.

Example 1: A method for preparing biomechanical pulp by hot steam in coordination with biological enzyme treatment and full utilization of by-product thereof. In this example, wheat strawland colored biomechanical pulp was prepared; at the same time, biomass compound fertilizer was prepared.

(1) Air-dried wheat straw after physical selection and dust removal was cut into 5 cm-long as raw materials, put into a wheat straw processor or reactor, and mixed with water according to a liquid ratio of 1:5 (g/mL), and a trace of KOH was added to a resulting mixture to adjust the pH of the wheat straw water to 14; the decaying leaves and straw that cannot be used for processing was collected.

(2) Hot steam whose temperature was 110° C. was charged for treatment for 20 min such that a small part of hemicellulose, lignin and pectin dissolved out from the wheat straw and the wheat straw was thermal-saturated and water-softened, with the pH of the softened-wheat-straw water at the end of the treatment being 8, and the waste lye was collected.

(3) The thermal-saturated and water-softened wheat straw was extruded on a screw extruder, and the pressure of the extruder was adjusted to make the wheat straw achieve a uniform and good splitting effect. The saturation, softening and splitting of the wheat straw were good, which was extruded once; the compression ratio of the screw extruder was 1:4, and the wastewater from the extrusion stage was collected.

(4) The softened and split wheat straw and an alkaline biological enzyme was reacted in a bioprocessor or a bioreactor at 50° C. for 50 min, the liquid ratio was 1:6 (g/mL), and the wheat straw was constantly stirred to allow the wheat straw and the biological enzyme fully reacted for further softening of the wheat straw fiber.

The alkaline biological complex enzyme was a complex enzyme of a xylanase, a cellulase and a pectinase with a total dosage of 60 IU/mL (1 ml of liquid with solid adding 60 IU of biological enzyme) and with a ratio of an enzyme activity of the xylanase, the cellulase and the pectinase being 5:3:1; the wastewater generated during the enzyme treatment stage was collected.

(5) The wheat straw after biological treatment was subjected to a two-stage refining with a refiner to make the pulp reach a beating degree of 42° SR.

The process parameters of the refining were as follows: a KPF high-consistency disc refiner was used for high-consistency refining, the spindle speed was 3000 r/min, the refining gap was 0.25 mm, and the refining washing water was collected.

(6) The refined wheat straw biomechanical pulp was disintegreted by a fiber disintegretor to make it uniformly mixed, and then prepared on a paper sheet former to form 120 g/m² linerboard paper. All physical indicators met the requirements for the production of unbleached linerboard and paper-based materials.

The waste lye, the wastewater from the extrusion stage, the wastewater generated in the enzyme treatment stage, and the refining washing water were mixed in a mass ratio of 10:1:5:15, then evaporated and concentrated by a multi-effect evaporator to obtain a residue, and heat energy was recycled for use in the hot steam pretreatment stage of step (1); the residue and the decaying leaves and straw that cannot be used for processing in step (1) were mixed according to 4:1 and phosphoric acid was added to adjust the pH to 7, then dried, crushed and granulated to produce biomass organic fertilizer.

Example 2: A method for preparing biomechanical pulp by hot steam in coordination with biological enzyme treatment and full utilization of by-product thereof. In this example, wheat strawland colored biomechanical pulp was prepared; at the same time, biomass compound fertilizer was prepared.

(1) Air-dried wheat straw after physical selection and dust removal was cut into 4 cm-long as raw materials, put into a wheat straw processor or reactor, and mixed with water according to a liquid ratio of 1:4 (g/mL), and a trace of KOH was added to a resulting mixture to adjust the pH of the wheat straw water to 14; the decaying leaves and straw that cannot be used for processing was collected.

(2) Hot steam whose temperature was 100° C. was charged for treatment for 30 min such that a small part of hemicellulose, lignin and pectin dissolved out from the wheat straw and the wheat straw was thermal-saturated and water-softened, with the pH of the softened-wheat-straw water at the end of the treatment being 9, and the waste lye was collected.

(3) The thermal-saturated and water-softened wheat straw was extruded on a screw extruder, and the pressure of the extruder was adjusted to make the wheat straw achieve a uniform and good splitting effect. The saturation, softening and splitting of the wheat straw were good, which was extruded once; the compression ratio of the screw extruder was 1:3, and the wastewater from the extrusion stage was collected.

(4) The softened and split wheat straw and an alkaline biological enzyme was reacted in a bioprocessor or a bioreactor at 55° C. for 60 min, the liquid ratio was 1:5 (g/mL), and the wheat straw was constantly stirred to allow the wheat straw and the biological enzyme fully reacted for further softening of the wheat straw fiber.

The alkaline biological complex enzyme was a complex enzyme of a xylanase, a cellulase and a pectinase with a total dosage of 60 IU/mL and with a ratio of an enzyme activity of the xylanase, the cellulase and the pectinase being 4:3:1.5; the wastewater generated during the enzyme treatment stage was collected.

(5) The wheat straw after biological treatment was subjected to a two-stage refining with a refiner to make the pulp reach a beating degree of 45° SR.

The process parameters of the refining were as follows: a KPF high-consistency disc refiner was used for high-consistency refining, the spindle speed was 3000 r/min, the refining gap was 0.2 mm, and the refining washing water was collected.

(6) The refined wheat straw biomechanical pulp was disintegrated by a fiber disintegretor to make it uniformly mixed, and then prepared on a paper sheet former to form 80 g/m² linerboard paper. All physical indicators met the requirements for the production of unbleached linerboard and paper-based materials.

The waste lye, the wastewater from the extrusion stage, the wastewater generated in the enzyme treatment stage, and the refining washing water were mixed in a mass ratio of 12:2:2:13, then evaporated and concentrated by a multi-effect evaporator to obtain a residue, and heat energy was recycled for use in the hot steam pretreatment stage of step (1); the residue and the decaying leaves and straw that cannot be used for processing in step (1) were mixed according to 5:2 and phosphoric acid was added to adjust the pH to 7, then dried, crushed and granulated to produce biomass organic fertilizer.

Example 3: A method for preparing biomechanical pulp by hot steam in coordination with biological enzyme treatment and full utilization of by-product thereof. In this example, wheat strawland colored biomechanical pulp was prepared; at the same time, biomass compound fertilizer was prepared.

(1) Air-dried wheat straw after physical selection and dust removal was cut into 6 cm-long as raw materials, put into a wheat straw processor or reactor, and mixed with water according to a liquid ratio of 1:6 (g/mL), and a trace of KOH was added to a resulting mixture to adjust the pH of the wheat straw water to 13; the decaying leaves and straw that cannot be used for processing was collected.

(2) Hot steam whose temperature was 110° C. was charged for treatment for 20 min such that a small part of hemicellulose, lignin and pectin dissolved out from the wheat straw and the wheat straw was thermal-saturated and water-softened, with the pH of the softened-wheat-straw water at the end of the treatment being 8, and the waste lye was collected.

(3) The thermal-saturated and water-softened wheat straw was extruded on a screw extruder, and the pressure of the extruder was adjusted to make the wheat straw achieve a uniform and good splitting effect. The saturation, softening and splitting of the wheat straw were good, which was extruded once; the compression ratio of the screw extruder was 1:4, and the wastewater from the extrusion stage was collected.

(4) The softened and split wheat straw and an alkaline biological enzyme was reacted in a bioprocessor or a bioreactor at 50° C. for 90 min, the liquid ratio was 1:5 (g/mL), and the wheat straw was constantly stirred to allow the wheat straw and the biological enzyme fully reacted for further softening of the wheat straw fiber.

The alkaline biological complex enzyme was a complex enzyme of a xylanase, a cellulase and a pectinase with a total dosage of 50 IU/mL and with a ratio of an enzyme activity of the xylanase, the cellulase and the pectinase being 6:3:1; the wastewater generated during the enzyme treatment stage was collected.

(5) The wheat straw after biological treatment was subjected to a one-stage refining with a refiner to make the pulp reach a beating degree of 38° SR.

The process parameters of the refining were as follows: a KPF high-consistency disc refiner was used for high-consistency refining, the spindle speed was 3000 r/min, the refining gap was 0.15 mm, and the refining washing water was collected.

(6) The refined wheat straw biomechanical pulp was disintegrated by a fiber disintegretor to make it uniformly mixed, and then prepared on a paper sheet former to form 60 g/m² linerboard paper. All physical indicators met the requirements for the production of unbleached linerboard and paper-based materials.

The waste lye, the wastewater from the extrusion stage, the wastewater generated in the enzyme treatment stage, and the refining washing water were mixed in a mass ratio of 6:1:3:7, then evaporated and concentrated by a multi-effect evaporator to obtain a residue, and heat energy was recycled for use in the hot steam pretreatment stage of step (1); the residue and the decaying leaves and straw that cannot be used for processing in step (1) were mixed according to 5:1 and phosphoric acid was added to adjust the pH to 7, then dried, crushed and granulated to produce biomass organic fertilizer.

Experimental Example 1: The method described in Example 1 was used but with the following specifications. The biological enzyme used after extrusion and splitting on a TSP360 thread rolling machine is adjusted to a complex enzyme using three enzymes: xylanase, cellulase and pectinase, the total dosage of which was 60 IU/mL, and the ratio of the enzyme activity was 3:2:1.5.

Experimental Example 2: The method described in Example 1 was used but with the following specifications. The biological enzyme used after extrusion and splitting on a TSP360 thread rolling machine was a complex enzyme of three enzymes xylanase, cellulase and pectinase with a total dosage of 60 IU/mL and with an ratio of the enzyme activity being 4:4:1.

Experimental Example 3: The method described in Example 1 was used but with the following specifications. The mass ratio of the waste lye, the wastewater from the extrusion stage, the wastewater generated in the enzyme treatment stage, and the refining washing water was 10:1:10:10.

Experimental Example 4: The method described in Example 1 was used but with the following specifications. The mass ratio of the waste lye, the wastewater from the extrusion stage, the wastewater generated in the enzyme treatment stage, and the refining washing water was 15:1:4:20.

Experimental Example 5: The method described in Example 1 was used but with the following specifications. The mass ratio of the residue and the decaying leaves and straw that cannot be used for processing in step (1) was 1:1.

Experimental Example 6: the method described in Example 1 was used but with the following specifications. The mass ratio of the residue and the decaying leaves and straw that cannot be used for processing in step (1) was 8:1.

Effect Verification:
1. Table 1 shows the comparison of the pulping physical properties of biomechanical pulp prepared in Example 1, Experimental Examples 1 and 2. It could be seen that the pulping physical properties of each group were good, meeting the requirements for the production of unbleached packaging paper and paper-based materials. The physical properties of Experimental Examples 3-6 were similar to that of Example 1.

TABLE 1

Comparison of pulping physical properties of the biomechanical pulp prepared by hot steam and biological enzyme treatment of wheat straw.

| Examples | Beating degree/°SR | Burst index/kPa · $m^2 \cdot g^{-1}$ | Tearing index/mN · $m^2 \cdot g^{-1}$ | Breaking length/km | Tensile index | Lateral folding endurance/times |
|---|---|---|---|---|---|---|
| Example 1 | 41 | 3.47 | 3.99 | 3.19 | 10.62 | 67 |
| Experimental Example 1 | 41 | 3.43 | 3.85 | 3.06 | 10.41 | 65 |
| Experimental Example 2 | 41 | 3.51 | 3.93 | 3.15 | 10.56 | 63 |

2. Biomass compound fertilizers prepared in Example 1, and Experiment Example 1-6 were used for fertilizer effect test.

(1) Experiment on Potting Corn

The biomass compound fertilizers prepared in Example 1, and Experimental Examples 1-6 were applied to potted corn for experiment. The biomass compound fertilizer (3 g/kg soil) was applied in the corn seedling stage. Compared with group CK, Example 1 and Experimental Examples 1-6 all significantly increased corn biomass, and Example 1 showed the best effect.

TABLE 2

| Examples | Biomass (g/pot) | Increase(%) |
|---|---|---|
| CK | 5.63 | — |
| Example 1 | 7.19 | 27.7 |
| Experimental Example 1 | 6.85 | 21.7 |
| Experimental Example 2 | 6.82 | 21.1 |
| Experimental Example 3 | 7.01 | 24.5 |
| Experimental Example 4 | 6.53 | 16.0 |
| Experimental Example 5 | 6.47 | 14.9 |
| Experimental Example 6 | 7.03 | 24.9 |

(2) Experiment on Potting Wheat

The biomass compound fertilizers prepared in Example 1, and Experimental Examples 1-6 were applied to potted wheat for experiment. The biomass compound fertilizer (5 g/kg soil) was applied in the wheat seedling stage. As shown in Table 3, compared with group CK with no fertilizer, Example 1 and Experimental Examples 1-6 all increased wheat biomass, and Example 1 showed the best effect.

TABLE 3

| Examples | Biomass (g/pot) | Increase(%) |
|---|---|---|
| CK | 8.35 | — |
| Example 1 | 10.14 | 21.4 |
| Experimental Example 1 | 9.68 | 16.0 |
| Experimental Example 2 | 9.41 | 12.7 |
| Experimental Example 3 | 9.96 | 19.3 |
| Experimental Example 4 | 9.25 | 10.8 |
| Experimental Example 5 | 9.06 | 8.5 |
| Experimental Example 6 | 9.93 | 18.9 |

3. Biomass compound fertilizers prepared in Example 1, and Experiment Examples 1-6 were used for storage stability test.

For a long time, the problem of agglomeration has affected the appearance of the compound fertilizer and brought inconvenience to the transportation and application of the compound fertilizer. Therefore, in this application, the storage stability (anti-caking performance) of the prepared biomass compound fertilizers was tested by the briquetting method at a temperature of 50° C. and under a pressure of 147N for 15 days. A 50 g compound fertilizer sample was placed in the ring, and the shear force data was measured on the cylindrical compound fertilizer briquettes. The test results are shown in Table 4. It could be seen that the storage stability of the biomass compound fertilizers prepared in this application was much higher than that of Experimental Examples 1-6.

TABLE 4

| Examples | Shear force(N) | Anti-caking rage(%) |
| --- | --- | --- |
| CK | 34.53 | 54.5 |
| Example 1 | 46.54 | 38.7 |
| Experimental Example 1 | 47.56 | 37.4 |
| Experimental Example 2 | 53.25 | 29.9 |
| Experimental Example 3 | 42.15 | 44.5 |
| Experimental Example 4 | 52.57 | 30.8 |
| Experimental Example 5 | 55.86 | 26.4 |
| Experimental Example 6 | 34.53 | 54.5 |

Note: Anti-caking rate=(blank shearing force-sample shearing force)/blank shearing force×100%, in which the blank shearing force was 75.92N.

Finally, it should be noted that the above descriptions are only preferred embodiments of the present disclosure and are not intended to limit the present disclosure. Although the present disclosure has been described in detail with reference to the foregoing embodiments, the technical solutions of which can be modified, or some of the technical features can be equivalently replaced for those skilled in the art. Any modification, equivalent replacement, improvement, etc. made within the spirit and principle of the present disclosure should be included in the protection scope of the present disclosure.

What is claimed is:

1. A method for preparing unbleached biomechanical pulp by treating wheat straw by hot steam in coordination with biological enzyme treatment and full utilization of by-products thereof, wherein the method comprises the following steps:
   (1) taking a waste wheat straw after wheat grain harvest as a raw material, mixing water with the wheat straw at a liquid ratio of 1:3-1:6, adding a trace of KOH to adjust a pH of a mixture of the wheat straw and the water to 10-14, and then charging hot steam whose temperature is 100-120° C. in a hot steam pretreatment stage for 15-60 minutes to obtain a wheat straw treated with the hot steam; collecting a waste lye and decaying leaves and straw that cannot be used for processing;
   (2) extruding and splitting the wheat straw treated with the hot steam in an extrusion stage to obtain a split wheat straw; collecting wastewater from the extrusion stage;
   (3) reacting the split wheat straw with an alkaline biological complex enzyme at a temperature of 40-60° C. for 30-90 minutes in an enzyme treatment stage to obtain a biologically treated wheat straw; collecting wastewater generated in the enzyme treatment stage; and
   (4) refining the biological treated wheat straw, and collecting a refining washing water; treating the waste lye, the wastewater from the extrusion stage, the wastewater generated in the enzyme treatment stage, and the refining washing water with a multi-effect evaporator to evaporate and concentrate to obtain a residue, and recycling heat energy for the hot steam pretreatment stage of step (1); mixing the residue with the decaying leaves and straw that cannot be used for processing in step (1) and adjusting pH thereof for fertilizer production.

2. The method of claim 1, wherein in step (1), the waste wheat straw is cut into 3-6 cm in length as a raw materials and air dried.

3. The method of claim 1, wherein in step (1), a pH of the wheat straw and the water reaches 7-9 at the end of the treatment.

4. The method of claim 1, wherein in step (2), a screw extruder is used for extruding and splitting, and a process condition is: a volumetric compression ratio of the screw extruder being 1:(3-6).

5. The method of claim 1, wherein in step (3), the liquid ratio is 1:3-8 (g/mL), and the alkaline biological complex enzyme is a complex enzyme of a xylanase, a cellulase and a pectinase with a total dosage of 10-80 IU/mL, and with a ratio of an enzyme activity of the xylanase, the cellulase and the pectinase being (0-6):(0-4):(0-1.5), none of the enzyme activity being 0.

6. The method of claim 1, wherein in step (4), times of the refining are determined according to production needs, and a beating degree of the refining is 25-50° SR.

7. The method of claim 1, wherein in step (4), refining process conditions are as follows: a disc refiner is used for refining, a spindle speed is 3000-4000 r/min, and a one- or two-stage refining is conducted, a refining gap is 0.15-0.5 mm.

8. The method of claim 1, wherein in step (4), a mass ratio of the waste lye, the wastewater from the extrusion stage, the wastewater generated in the enzyme treatment stage, and the refining washing water is 5-12:1-5:1-5:5-15;
   a mass ratio of the residue to the decaying leaves and straw that cannot be used for processing in step (1) is 4-7:1-2;
   adjusting pH for fertilizer production is as follows: adding phosphoric acid to adjust the pH to 7, drying, pulverizing and granulating.

9. The method of claim 1, wherein in step (3), the liquid ratio is 1:3-8 (g/mL), and the alkaline biological complex enzyme is a complex enzyme of a xylanase, a cellulase and a pectinase with a total dosage of 10-50 IU/mL, and with a ratio of an enzyme activity of the xylanase, the cellulase and the pectinase being (5-6):(2-3):1.

* * * * *